(12) United States Patent
Saksela

(10) Patent No.: US 8,735,328 B2
(45) Date of Patent: May 27, 2014

(54) FUSION POLYPEPTIDE FOR DETECTION OF CONSERVED COMBINATORIAL OR COMPOSITE EPITOPES IN NON-CONSERVED PROTEINS

(75) Inventor: Kalle Saksela, Helsinki (FI)

(73) Assignee: Next Biomed Technologies NBT Oy, Helsinki (FI)

( * ) Notice: Subject to any disclaimer, the term of this patent is extended or adjusted under 35 U.S.C. 154(b) by 1230 days.

(21) Appl. No.: 12/530,019

(22) PCT Filed: Mar. 7, 2008

(86) PCT No.: PCT/FI2008/050111
§ 371 (c)(1),
(2), (4) Date: Dec. 18, 2009

(87) PCT Pub. No.: WO2008/107523
PCT Pub. Date: Sep. 12, 2008

(65) Prior Publication Data
US 2010/0190655 A1    Jul. 29, 2010

Related U.S. Application Data

(60) Provisional application No. 60/893,420, filed on Mar. 7, 2007.

(30) Foreign Application Priority Data

Mar. 7, 2007 (FI) ..................... 20075159

(51) Int. Cl.
C40B 30/04        (2006.01)
(52) U.S. Cl.
USPC ....................................... 506/9

(58) Field of Classification Search
None
See application file for complete search history.

(56) References Cited

U.S. PATENT DOCUMENTS

2003/0027247 A1    2/2003    Wang et al.

FOREIGN PATENT DOCUMENTS

WO    WO 02/20554 A2    3/2002
WO    WO-02/055718 A2   7/2002

OTHER PUBLICATIONS

Moore et al. (Mar. 1996) Journal of Virology vol. 70 pp. 1863-1872.*
Yu et al. (1996) Virology vol. 222 vol. 289-292.*
Combita et al. (Jul. 2002) Journal of Virology vol. 76 pp. 6480-6486.*
Fagerstam et al. (1990) Journal of Molecular Recognition vol. 3 pp. 208-214.*
Barbas et al. (Apr. 5, 1993) Journal of Molecular Biology vol. 230 pp. 812-823.*
Yang et al. (1995) Journal of Molecular Biology vol. 254 pp. 392-403.*
Andris-Widhopf et al. (Aug. 2000) Journal of Immunological Methods vol. 242 pp. 159-181.*
Dehaard, H.J.W. et al.; Selection of recombinant, library-derived antibody fragments against p24 for human immunodeficiency virus type 1 diagnostics. Clin. Diagn. Lab. Immunol. 1998, vol. 5, No. 5, p. 636-644.

(Continued)

*Primary Examiner* — Christian Boesen
(74) *Attorney, Agent, or Firm* — Birch, Stewart Kolasch & Birch, LLP

(57) ABSTRACT

The present invention provides multiepitope-binding fusion polypeptides for use in a method for the detection of the presence of human immunodeficiency virus, HIV, in a biological sample. The present invention also provides a method for producing multiepitope-binding fusion polypeptides.

6 Claims, 1 Drawing Sheet

```
     3  5  5 534    4     421311221       3  35 332
     PIVQNLQGQMVHQAISPRTLNAWVKVVEEKAFSPEVIPM 3          4  3  5 234   3343 2  2 34    415132
     FSALSEGATPQDLNTMLNTVGGHQAAMQMLKETINEEAA 113 21     22   541 2  352211   2  34    532   2
       EWDRLHPVHAGPIAPGQMREPRGSDIAGTTSTLQEQIGW 41  445 212 32    13    12235    2242  51142  13
     MTHNPPIPVGEIYKRWIILGLNKIVRMYSPTSILDIRQG 22  422223342      31212    3  23  222  222  22 2
      PKEPFRDYVDRFYKTLRAEQASQEVKNWMTETLLVQNAN 121   31    32   2    2212422232222  2124  2
      PDCETILKALGPGATLEEMMTACQGVGGPGHKARVL
```

(56) References Cited

OTHER PUBLICATIONS

Lu, D. et al.; Fab-scFv fusion protein; an efficient approach to production of bispecific antibody fragments. J. Immunol. Methods 2002, vol. 267, p. 213-226.

Neri, D. et al.; High-affinity antigen binding by chelating recombinant antibodies (CRAbs). J. Mol. Biol. 1995, vol. 246, p. 367-373.

Janvier et al., "Linear B-cell epitopes of the major core protein of human immunodeficiency virus types 1 and 2," Journal of Virology, 1990, vol. 64, No. 9, pp. 4528-4263.

Kurle et al., "Full-length gag Sequences of HIV Type 1 Subtype C Recent Seroconverters from Pune, India," Aids Research and Human Retroviruses, vol. 20, No. 10, 2004, pp. 1113-1118.

Persson et al., "A Focused Antibody Library for Improved Hapten Recognition," J. Mol. Biol., 2006, vol. 357, pp. 607-620.

Schupbach et al, "Antiretroviral Treatment Monitoring With an Improved HIV-1 p24 Antigen Test: An Inexpensive Alternative to Tests for Viral RNA," Journal of Medical Virology, 2001, vol. 65, pp. 225-232.

US Office Action for U.S. Appl. No. 12/522,838, dated Apr. 18, 2012.

US Office Action for U.S. Appl. No. 12/522,838, dated Feb. 22, 2013.

\* cited by examiner 3 5 5 534 4 421311221 3 35 332
PIVQNLQGQMVHQAISPRTLNAWVKVVEEKAFSPEVIPM 3 4 3 5 234 3343 2 2 34 415132
FSALSEGATPQDLNTMLNTVGGHQAAMQMLKETINEEAA 113 21 22 541 2 352211 2 34 532 2
EWDRLHPVHAGPIAPGQMREPRGSDIAGTTSTLQEQIGW 41 445 212 32 13 12235 2242 51142 13
MTHNPPIPVGEIYKRWIILGLNKIVRMYSPTSILDIRQG 22 4222223342 31212 3 23 222 222 22 2
PKEPFRDYVDRFYKTLRAEQASQEVKNWMTETLLVQNAN

121 31 32 2 2212422232222 2124 2
PDCETILKALGPGATLEEMMTACQGVGGPGHKARVL

SEQUENCE LISTING

<160> NUMBER OF SEQ ID NOS: 8

<210> SEQ ID NO 1
<211> LENGTH: 231
<212> TYPE: PRT
<213> ORGANISM: Human immunodeficiency virus

<400> SEQUENCE: 1

Pro Ile Val Gln Asn Leu Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr

-continued

```
               35                   40                  45
Pro Gln Asp Leu Asn Thr Met Leu Asn Thr Val Gly Gly His Gln Ala
 50                  55                  60
Ala Met Gln Met Leu Lys Glu Thr Ile Asn Glu Glu Ala Ala Glu Trp
 65                  70                  75                  80
Asp Arg Leu His Pro Val His Ala Gly Pro Ile Ala Pro Gly Gln Met
                 85                  90                  95
Arg Glu Pro Arg Gly Ser Asp Ile Ala Gly Thr Thr Ser Thr Leu Gln
                100                 105                 110
Glu Gln Ile Gly Trp Met Thr His Asn Pro Pro Ile Pro Val Gly Glu
                115                 120                 125
Ile Tyr Lys Arg Trp Ile Ile Leu Gly Leu Asn Lys Ile Val Arg Met
                130                 135                 140
Tyr Ser Pro Thr Ser Ile Leu Asp Ile Arg Gln Gly Pro Lys Glu Pro
145                 150                 155                 160
Phe Arg Asp Tyr Val Asp Arg Phe Tyr Lys Thr Leu Arg Ala Glu Gln
                165                 170                 175
Ala Ser Gln Glu Val Lys Asn Trp Met Thr Glu Thr Leu Leu Val Gln
                180                 185                 190
Asn Ala Asn Pro Asp Cys Glu Thr Ile Leu Lys Ala Leu Gly Pro Gly
                195                 200                 205
Ala Thr Leu Glu Glu Met Met Thr Ala Cys Gln Gly Val Gly Gly Pro
                210                 215                 220
Gly His Lys Ala Arg Val Leu
225                 230

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Asn Ala Trp Val Lys
 1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Phe Arg Asp Tyr
 1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Arg Ala Glu Gln
 1

<210> SEQ ID NO 5
<211> LENGTH: 4
```

-continued

```
<212> TYPE: PRT
<213> ORGANISM: Artificial Sequence
<220> FEATURE:
<223> OTHER INFORMATION: Synthetic peptide

<400> SEQUENCE: 5

Asn Pro Asp Cys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Val Gly Gly Pro
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide

<400> SEQUENCE: 7

Ala Trp Val Lys
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Asn Ala Trp Val
1
```

FUSION POLYPEPTIDE FOR DETECTION OF CONSERVED COMBINATORIAL OR COMPOSITE EPITOPES IN NON-CONSERVED PROTEINS

This application is the National Phase of PCT/FI2008/050111 filed on Mar. 7, 2008, which claims priority under 35 U.S.C. 119(e) to U.S. Provisional Application No. 60/893,420 filed on Mar. 7, 2007, and under 35 U.S.C. 119(a) to Patent Application No. 20075159 filed in Finland on Mar. 7, 2007, all of which are hereby expressly incorporated by reference into the present application.

FIELD OF THE INVENTION

The present invention provides a fusion polypeptide for reliable diagnostic detection of highly variable proteins that lack conserved antibody binding epitopes. This is achieved via recognition of independent but linked structural determinants in the same target protein using polypeptides comprised of two or more binding units. The structural determinants targeted with this approach consist of short (3-5 residues) conserved amino acid sequences in these otherwise variable proteins. These tri-, tetra-, and pentapeptides can be efficiently targeted using bioengineered high affinity binding polypeptides (BHAP), but since such short sequences may appear in many other proteins in the specimens of interests, e.g. serum samples, the diagnostic value of this binding is of limited value. However, cooperative binding of multiepitope-binding fusion polypeptides (MEBIP) comprised of two or more BHAPs that bind to multiple conserved tri-, tetra-, or pentapeptides can be used to overcome this problem, and to ensure specific targeting of the protein of interest with a superior affinity that enables diagnostic detection of the said protein. Recombinant antibody fragment is one example of several types of binding proteins that could represent one or all BHAP subunits in a MEBIP. As a consequence, this invention provides a novel means for reliable and quantitative detection of proteins encoded by viruses with high mutational capacities, such as HIV.

BACKGROUND OF THE INVENTION

Schupbach et al. (Journal of Medical Virology, 2001, 65:225-232) discloses that heat-denatured, amplification-boosted p24 antigen can be used as an alternative to HIV RNA testing in order to monitor the treatment of HIV infection. Respess et al. (Journal of Clinical Microbiology, 2005, 43(1): 506-508) and Knuchel et al. (Journal of Clinical Virology, 2006, 36:64-67) also disclose ultrasensitive p24 antigen assays as an alternative to HIV RNA testing.

Boder et al. (PNAS, 2000, 97(20):10701-10705) discloses directed evolution of antibody fragments with monovalent femtomolar antigen-binding affinity. Holliger and Hudson (Nature Biotechnology, 2005, 23(9):1126-1136) reviews engineered antibody fragments. Nygren and Uhlen (Current Opinion in Structural Biology, 1997, 7:463-469) and Hosse et al. (Protein Science, 2006, 15:14-27) review engineering of protein display scaffolds for molecular recognition.

Binz et al. (Nature Biotechnology, 2005, 23(10):1257-1268) and Hey et al. (Trends in Biotechnology, 2005, 23(10): 514-422) review engineering of novel binding proteins from nonimmunoglobulin domains.

Bi-specific recombinant antibody molecules that can recognize and bring together two different ligands are well-known in the literature (see e.g., Albrecht et al., J Immunol Meth 310: 100-16, 2006). Bi-specific recombinant antibodies that bind to two different epitopes in the same protein have also been described (see e.g. Neri et al., J Mol Biol 246: 367-73, 1995; Zhou, J Mol Biol 329: 1-8, 2003). The combinatorial binding resulted in a significant increase in binding affinity compared to binding of each of the two recombinant antibodies alone. While MEBIPs may have similarities with construction of bi-specific recombinant antibodies, it is important to appreciate that the present innovation is novel and unrelated to the described design and use of bi-specific recombinant antibodies.

Although helpful, the increased affinity involved in cooperative binding of more than one covalently joined BHAP (whether a recombinant antibodies or another type of molecule) is not the reason for targeting multiple regions in the protein of interest. Instead, the key idea of this innovation is to combine scattered short conserved peptides within a variable protein to a "virtual epitope" that provides sufficient complexity for diagnostic specificity in detection. To provide such structural complexity a linear peptide epitope should consist of at least six residues. However, a look into available sequence databases shows that well conserved continuous 6-residues amino acids stretches are hard to find in many highly variable microbial proteins, in particular those of RNA viruses. For example, the HIV-1 p24 protein does not contain a single hexapeptide (6-mer) that would be conserved in more than 99% of known HIV-1 sequences, which makes its reliable immunological detection problematic. As discussed below, coordinated detection of combinations of conserved tri-, tetra-, or pentapeptides using the MEBIP approach can help to solve this problem. Thus, this novel approach therefore allows development of better means for diagnostic detection of highly variable microbial proteins, such as HIV-1 p24.

BRIEF DESCRIPTION OF THE DRAWING

FIG. 1. Amino acid sequence of p24 protein of a representative HIV-1 strain (SEQ ID NO:1). The FIGURE shows relative conservation of the residues of p24 among clades A-K and various circulating recombinant viruses of the predominant M-type of HIV-1 as well as O- and N-type viruses and related SIV viruses from chimpanzees. Score of 1 indicates conservation of more than 99.75%, score of 2 indicates conservation of >99.50%, score of 3 indicates conservation of >99.00%, score of 4 indicates conservation of >98.00%, and score of 5 indicates conservation of >97.00% (the score is shown above each residue). Residues that are less than 97% conserved are not scored. Continuous peptide stretches with an overall conservation of >99.00% are underlined and indicated in boldface.

DETAILED DESCRIPTION OF THE INVENTION

The following definitions are provided for some terms used in this specification.

"Antibody" in its various grammatical forms is used herein as a collective noun that refers to a population of immunoglobulin molecules and/or immunologically active portions of immunoglobulin molecules, i.e., molecules that contain an antigen binding site or a paratope.

An "epitope" is the part of a macromolecule, such as polypeptides, that is recognized by the immune system, specifically by antibodies, B cells, or cytotoxic T cells. Most epitopes recognized by antibodies can be thought of as three-dimensional surface features of an antigen molecule. These surfaces fit precisely and thus bind to antibodies. These surfaces may depend on tertiary protein structure, such that residues that form an epitope are positioned apart from each other in the amino acid sequence of a protein (conformational epitopes), or may be formed by continuous peptide regions within a protein (linear epitopes). Therefore, if a protein is denatured, as often is the case in diagnostic use of antibodies, only linear epitopes can be used for detection. The number of consecutive amino acid residues that form a linear epitope recognized by an antibody varies, but typically ranges from six to ten (6-10). However, natural antibodies can recognize shorter epitopes with significant affinities, and recombinant antibodies can be targeted to bind even to a single amino acid residue.

An "antigen-binding site", a "paratope", is the structural portion of an antibody molecule that specifically binds an antigen.

"Single-chain antibody" (scFv) is used to define a molecule in which the variable domains of the heavy and light chain of an antibody are joined together via a linker peptide to form a continuous amino acid chain synthesised from a single mRNA molecule (transcript).

"Immunoassay" is a biochemical test that measures the level of a substance in a biological liquid, typically serum, plasma, urine, or other body fluids, using the reaction of an antibody or antibodies to its antigen. The assay uses the specific binding of an antibody to its antigen. Monoclonal antibodies are often used because they usually bind to a single site of a molecule to be detected, and therefore provide more specific and accurate testing, which is not interfered by other molecules in the sample. The antibodies used must have a high affinity for the antigen. The presence of the antigen can be measured for instance in the diagnosis of infectious diseases by detecting the microbe specific molecular structures. Detecting the quantity of the antigen can be achieved by a variety of methods. One of the most common used techniques is to label the antigen or antibody. The label may consist of an enzyme (Enzyme ImmunoAssay, EIA), fluorescence (FIA), luminescence (LIA) or they can be based on agglutination, nephelometry, turbidimetry or immunoblotting (Western Blot).

Immunoassays can be either competitive or non-competitive, and they can be homogeneous or heterogeneous. In a competitive assay, the antigen in the sample competes with the labelled antigen to bind with antibodies. The amount of labelled antigen bound to the antibody site is then measured. The response will be inversely proportional to the concentration of antigen in the sample, because the greater the response, the less antigen in the sample is available to compete with the labelled antigen.

In non-competitive immunoassays, often referred to as "sandwich assay", antigen in the sample is bound to the "capture" antibody and the amount of the labelled antibody on the site is measured. Unlike in the case of competitive assay the result will be directly proportional to the concentration of the antigen.

A heterogeneous immunoassay will require an extra step to remove unbound antibody or antigen from the site, usually using a solid phase material. Homogenous assays do not require the separation phase to remove the unbound antibody or antigen molecules. Immunoassays have a particularly important role in the diagnosis of HIV.

The abbreviation "MEBIP" refers to "multiepitope-binding fusion polypeptides", which are genetically engineered protein constructs comprising two or more independent binding units that bind to different sites in a common target protein. One or more of the binding units within a MEBIP may be a scFv.

The "virtual epitope" is a structure typically formed by two stretches of three to five amino acid residues that tend to be constant even in otherwise highly variable proteins, such as many viral proteins, and can serve as a ligand for a MEBIP. "Virtual epitope" may overlap with an antigenic epitope, but may not be targeted by a traditional antibody.

As used herein, the term "specifically binding", or "specifically recognizing", or the expression "having binding specificity to an epitope" refers to a low background and high affinity binding between a MIEBIP or a fragment or derivative thereof and its target molecule (i.e. lack of non-specific binding). In other words, the terms (and equivalent phrases) refer to the ability of a binding moiety (e.g., a receptor, antibody, ligand or antiligand) to bind preferentially to a particular target molecule (e.g., ligand or antigen) in the presence of a heterogeneous population of proteins and other biologics (i.e., without significant binding to other components present in a test sample). Typically, specific binding between two entities, such as a ligand and a receptor, means a binding affinity of at least about $10^6$ $M^{-1}$, and preferably at least about $10^7$, $10^8$, $10^9$, or $10^{10}$ $M^{-1}$, more preferably at least about $10^{11}$, $10^{12}$, $10^{13}$, $10^{14}$, or $10^{15}$ $M^{-1}$.

The terms "specificity" or "high specificity" may also refer to the capacity of a binding polypeptide, such as MEBIP, to bind to 95%, 95.5%, 96%, 96.5%, 97%, 97.5%, 98%, 98.5%, 99%, 99.5% or 100% of the variants of its non-conserved polypeptide ligand.

The terms "biopanning" and "phage display library" are used herein in the same way as in the US Patent Application No. 2005/0074747 (Arap et al.).

Further, the classic definition of an antigen is "any foreign substance" that elicits an immune response (e.g., the production of specific antibody molecules) when introduced into the tissues of a susceptible animal and is capable of combining with the specific antibodies formed. Antigens are generally of high molecular weight and commonly are proteins or polysaccharides. Polypeptides, lipids, nucleic acids and many other materials can also function as antigens. Immune responses may also be generated against smaller substances, called haptens, if these are chemically coupled to a larger carrier protein, such as bovine serum albumin, keyhole limpet hemocyanin (KLH) or other synthetic matrices. A variety of molecules such as drugs, simple sugars, amino acids, small peptides, phospholipids, or triglycerides may function as haptens. Thus, given enough time, just about any foreign substance will be identified by the immune system and evoke specific antibody production. However, this specific immune response is highly variable and depends much in part on the size, structure and composition of antigens. Antigens that elicit strong immune responses are said to be strongly immunogenic.

Characteristics of a good antigen include:
Areas of structural stability and chemical complexity within the molecule.
Significant stretches lacking extensive repeating units.
A minimal molecular weight of 8,000-10,000 Daltons, although haptens with molecular weights as low as 200 Da have been used in the presence of a carrier protein.
The ability to be processed by the immune system.
Immunogenic regions which are accessible to the antibody-forming mechanism.
Structural elements that are sufficiently different from the host.
For peptide antigens, regions containing at least 30% of immunogenic amino acids: K, R, E, D, Q, N.
For peptide antigens, significant hydrophilic or charged residues.
Because an antibody binding epitope can consist of only a few amino acids it may not have any diagnostic value, because the same epitope may be present in many other proteins in the same specimen (e.g. a serum sample). Thus, an epitope useful, e.g., in detection of microbial proteins in human blood should not be present in human serum, which has been estimated to include up to 10,0000 different proteins. When assuming that the average size of a serum protein would be 50 kD (approximately 500 amino acids), and that all 20 natural amino acids would be equally used in human proteins, the likelihood of any given di- tri- or tetrapeptide to be found in serum can be calculated to be essentially 100%. The corresponding likelihood of a given pentapeptide (5 amino acids) to be present among a set of 10,000 hypothetical 50 kD proteins is 79%, and the likelihood of a hexapeptide (6 amino acids) being present is 7.5%.

Thus, it can be estimated that the diagnostic utility of 79% of all 5-mer and 7.5% of all 6-mer antibody epitopes in microbial pathogens is compromised by their presence in normal serum. In other words, only 21% antibodies (or other types of specific binding proteins) capable of binding sufficiently tightly to a microbial protein via recognizing a 5-mer linear peptide epitope can be expected not to bind to an epitope present in human serum and thus be useful for diagnostic detection of this microbe. By comparison, the great majority of antimicrobial antibodies that recognize linear epitope consisting of six or more residues does not have this problem. Of course, the utility of diagnostic antibodies may also be compromised because they cross-react with epitopes that are encoded by unrelated peptide sequences, but the length of the target epitope is less relevant in the case of this complication.

Based on the above calculations, it is evident that linear epitopes consisting of five residues have only limited value, and epitopes shorter than five residues are not useful as detection targets in microbial diagnostics. However, the situation is different if the combinatorial presence of such short epitopes in a single protein is considered. The calculated likelihood of appearance of different combinations of tri-, tetra-, and pentapeptides in a single protein among 1000 or 10,000 hypothetical 500 residue-long polypeptides is shown below (Table 1).

TABLE 1

| Epitope combination | Chance of being present in 1000 50 kD proteins | Chance of being present in 10,000 50 kD proteins |
| --- | --- | --- |
| Tripeptide + tripeptide | 97% | ~100% |
| Tripeptide + tetrapeptide | 17% | 85% |
| Tripeptide + pentapeptide | 0.94% | 9.0% |
| Tetrapeptide + tetrapeptide | 1.0% | 9.3% |
| Tetrapeptide + pentapeptide | 0.05% | 0.5% |
| Pentapeptide + pentapeptide | ~0% | 0.02% |

This analysis shows that epitopes as short as three or four residues could be very useful for diagnostic purposes if their combined presence with another epitope of suboptimal length (tetra- or pentamers) could be detected. Together such short and thereby non-diagnostic epitopes could be considered as diagnostically valuable "virtual epitopes". This concept could be highly useful when trying to reliably detect highly variable microbial proteins, such as HIV p24 antigen, which contain few amino acid residues that would be positioned next to each other and conserved in most viral strains and quasispecies.

Based on the above, the present invention provides a method for producing a fusion polypeptide, i.e. a MEBIP, capable of specifically binding simultaneously to at least two epitopes of a polypeptide antigen known to be variable, said continuous epitopes consisting of 3, 4 or 5 adjacently positioned conserved amino acid residues of said antigen, the method comprising the steps of:

a) selecting of 3 to 5 amino acid long conserved regions in the antigen by computational analysis of known amino acid sequences of the antigen;

b) preparing a peptide based on the selected conserved region of the antigen;

c) contacting a library of particles expressing binding proteins, such as a phage library of single chain antibodies, with said peptide;

d) isolating those particles which express binding proteins having binding activity towards said peptide;

e) subjecting nucleic acid obtained or derived from the particle(s) isolated in step d) to mutagenesis;

f) preparing a library of particles expressing binding proteins based on the particles obtained from step e);

g) contacting a library obtained from step f) with said peptide or fragment thereof;

h) isolating those particles which express binding proteins having improved binding activity towards said peptide or a fragment thereof;

i) repeating steps e) to h) one or more times;

j) obtaining particles which are able to specifically bind to an at least 3 to 5 adjacent or non-contiguous amino acids long epitope in said antigen from the particles obtained from step i);

k) preparing said fusion polypeptide based on the particles isolated in step j) by combining into one fusion polypeptide the binding specificity of two of said particles having specificity to at least two different epitopes of said antigen resulting in a fusion polypeptide having high specificity with regard to variants of said antigen.

Preferably the MEBIP obtained in step k) specifically binds to 95%, 95.5%, 96%, 96.5%, 97%, 97.5%, 98%, 98.5%, 99%, or more than 99% of the variants of said antigen, which preferably is the p24 polypeptide of HIV.

Preferably said peptide in step b) is selected from 3 to 5 amino acid long regions of the conserved peptides of the p24 polypeptide of HIV consisting of: NAWVK (SEQ ID NO: 2), FRDY (SEQ ID NO: 3), RAEQ (SEQ ID NO: 4), NPDC (SEQ ID NO: 5), VGGP (SEQ ID NO: 6), AWVK (SEQ ID NO: 7), NAWV (SEQ ID NO: 8), RDY, FRD, AEQ, RAE, PDC, NPD, GGP, VGG, WVK, AWV, NAW, SDI, PVG, GLN, WMT, TLL, EMM, and HKA.

The present invention is also directed to a fusion polypeptide, i.e. a MEBIP, capable of specifically binding simultaneously to at least two epitopes of a polypeptide antigen known to be variable, said epitopes consisting of 3 to 5 residues long stretches of conserved amino acid residues of said antigen, and said polypeptide having high specificity with regard to variants of said antigen. Such MEBIP can be obtained by the method described above.

HIV Assay

In the case of detection of human immunodeficiency virus, HIV, the problem is that the antigenic sites of the virus are constantly and rapidly changing. The solution of the present invention is to provide means to prepare a MEBIP, which specifically binds to two different amino acid stretches consisting of highly conserved 3 to 5 amino acid residues long epitopes of the p24 polypeptide, which would be difficult or impossible to accomplish with conventional antibodies. The MEBIPs thus obtained can be used in detection methods in the same way as antibodies and are thus useful in detecting the presence of human immunodeficiency virus in a biological sample.

A person skilled in the art can easily apply the above approach also to other antigen assays. Thus, the present invention provides a general method for detecting the presence of an antigen in a biological sample, the method comprising
a) contacting said sample or a fraction thereof with a MEBIP; and
b) detecting a complex of said polypeptide and antigen, the presence of said complex indicating the presence of said antigen in said sample.

Preferably, said antigen is the p24 polypeptide of HIV and the method is for the detection of HIV in the sample.

The publications and other materials used herein to illuminate the background of the invention, and in particular, to provide additional details with respect to its practice, are incorporated herein by reference. The present invention is further described in the following examples, which are not intended to limit the scope of the invention.

EXAMPLES

Example 1

To identify conserved regions useful as virtual epitopes in HIV p24 a large number of individual amino acid sequence available in public databases, such as http://www.hiv.lanl.gov/content/index, were aligned with each other, and the relative conservation of each amino acid residue was evaluated. Based on this analysis peptide stretches consisting of three or more residues conserved in more than 99% of the sequences were selected for further analysis (see FIG. 1).

Synthetic peptides containing one or several potential conserved regions for virtual epitopes in p24 of HIV, are used to screen large libraries of polypeptides that can serve as MEBIP precursors using affinity based selection methods. For example, the ETH-2-Gold phage display library generated by Neri and colleagues (Proteomics 5:2340-2350, 2005) containing three billion individual recombinant antibody clones is screened for polypeptides that can specifically interact with conserved regions-containing peptides. Several libraries containing potential ligand binding polypeptides based on non-Ig-derived polypeptides also exist (see e.g. Nature Biotechnology 23:1257-1268, 2005) or can be designed de novo, and are used to screen for polypeptides as to develop MEBIPs. In addition to screening of such MEBIP precursor libraries with synthetic peptides, recombinant proteins containing one or more potential conserved regions, as well as denatured HIV capsid proteins (p24) are used as ligands in affinity selection.

In the latter case targeting of the binding to peptides with said conserved regions can be achieved for example via use of these peptides to elute phages with desired binding specificities.

Following generation of potential MEBIP molecules that bind to these peptides, for example by screening scFv phage libraries (basic principles of screening recombinant antibody libraries are reviewed by Hoogenboom, Nature Biotechnology 23(9):1105-1116), the residues that account for this binding are confirmed using peptide array technology. Any combination of two or more of the epitopes shown in FIG. 1 is a potential combinatorial target for MEBIP binding to be used in detection of HW p24.

Example 2

MEBIP precursors that bind both to denatured p24 as well as a defined virtual epitope-containing peptide are chosen for further development. Binding affinity of these pre-MEBIPs is maximized via reiterated mutagenesis and affinity selection, as described by the inventors in their previous studies related to SCA engineering (Biochemistry 41:12729-12738, 2003). Both random mutagenesis using error-prone PCR as described in Biochemistry article cited above or other similar techniques, as well as targeted mutagenesis of the binding surfaces in the pre-MEBIPs, or combinations of these approaches are used. Traditional phage-display based on the M13-derived phagemid plus helper bacteriophage-mediated approach are used for affinity selection and amplification of the improved pre-MEBIP molecules, but other related screening methods can also be used.

Subsequently, a MEBIP is prepared (see e.g., Albrecht et al., 2006, Journal of Immunological Methods 310:100-116) by combining into one fusion polypeptide the binding specificity of two of the pre-MEBIPs having specificity to conserved regions of a virtual epitope in p24 resulting in a fusion polypeptide, a MEBIP. Finally, binding affinity of the assembled MEBIP towards its composite target is further optimized using the same methodology as initially used to engineer binding properties of the pre-MEBIP subunits.

The binding affinities and other salient properties are then characterized in detail. The properties of optimal MEBIPs, which are used as such or as various fusion protein derivatives for building of novel p24 detection assays include: 1) High affinity for heat-denatured HIV p24 protein, preferably meaning a dissociation constant lower than $10^{-12}$M, 2) absolute conservation of the virtual epitope in more than 99% of the relevant virus strains, and 3) good solubility and ease of large-scale recombinant production.

The invention claimed is:

1. A method for producing a fusion polypeptide capable of specifically binding simultaneously to at least two epitopes of a polypeptide antigen known to be variable, said epitopes consisting of 3 to 5 adjacent conserved amino acid residues of said antigen, the method comprising the steps of:
   a) selecting 3 to 5 amino acid long conserved regions in the antigen by computational analysis of known amino acid sequences of the antigen, wherein said antigen is the p24 polypeptide of HIV, and wherein said peptide is selected from the 3 to 5 amino acid long regions of the antigen and wherein the peptide is selected from the group consisting of: NAWVK (SEQ ID NO: 2), FRDY (SEQ ID NO: 3), RAEQ (SEQ ID NO: 4), NPDC (SEQ ID NO: 5), VGGP (SEQ ID NO: 6), AWVK (SEQ ID NO: 7), NAWV (SEQ ID NO: 8), RDY, FRD, AEQ, RAE, PDC, NPD, GGP, VGG, WVK, AWV, NAW, SDI, PVG, GLN, WMT, TLL, EMM, and HKA;

b) preparing peptides selected is step a);

c) contacting a library of particles expressing binding proteins with one or more of said peptides;

d) isolating those particles which express binding proteins having binding activity towards the peptides;

e) subjecting nucleic acid obtained or derived from the particle(s) isolated in step d) to mutagenesis;

f) preparing a library of particles expressing binding proteins based on the particles obtained from step e);

g) contacting a library obtained from step f) with one or more of said peptides or fragment thereof;

h) isolating those particles which express binding proteins having improved binding activity towards said peptides or a fragment thereof;

i) repeating steps e) to h) one or more times;

j) obtaining particles which are able to specifically bind to an at least 3 to 5 adjacent amino acids long epitope in said antigen from the particles obtained from step i);

k) preparing said fusion polypeptide based on the particles isolated in step j) by combining into one fusion polypeptide the binding specificity of two of said particles having specificity to at least two different epitopes of said antigen resulting in a fusion polypeptide having high specificity with regard to variants of said antigen.

2. The method according to claim 1, wherein said fusion polypeptide obtained in step k) specifically binds to 95%, 95.5%, 96%, 96.5%, 97%, 97.5%, 98%, 98.5%, 99%, 99.5% or 100% of the variants of said antigen.

3. The method according to claim 1, wherein said library is a phage library of single chain antibodies.

4. The method according to claim 1, wherein the epitopes consist of 3 to 4, or 4 to 5, adjacent amino acid residues.

5. The method according to claim 1, wherein one or both epitopes consist of 3,4, or 5 adjacent amino acid residues.

6. The method according to claim 1, wherein said fusion polypeptide has affinity of $10^{-12}$ to $10^{-15}$ M to the antigen.

* * * * *